(12) United States Patent
Treado et al.

(10) Patent No.: US 6,965,793 B2
(45) Date of Patent: *Nov. 15, 2005

(54) METHOD FOR RAMAN CHEMICAL IMAGING OF ENDOGENOUS CHEMICALS TO REVEAL TISSUE LESION BOUNDARIES IN TISSUE

(75) Inventors: Patrick J. Treado, Pittsburgh, PA (US); Matthew P. Nelson, Pittsburgh, PA (US)

(73) Assignee: ChemImage Corporation, Pittsburgh, PA (US)

(*) Notice: Subject to any disclaimer, the term of this patent is extended or adjusted under 35 U.S.C. 154(b) by 149 days.

This patent is subject to a terminal disclaimer.

(21) Appl. No.: 10/184,580

(22) Filed: Jun. 28, 2002

(65) Prior Publication Data

US 2003/0004419 A1    Jan. 2, 2003

Related U.S. Application Data

(60) Provisional application No. 60/301,708, filed on Jun. 28, 2001.

(51) Int. Cl.[7] .............................................. A61B 6/00
(52) U.S. Cl. ...................... 600/476; 600/407; 600/473; 600/477; 600/310; 600/318; 356/301; 356/303; 606/2; 606/3; 606/4; 606/10
(58) Field of Search ............................... 600/472–478, 600/310, 312, 407, 318; 356/450, 451, 456, 356/460, 301, 303; 606/2–4, 10

(56) References Cited

U.S. PATENT DOCUMENTS

| | | | |
|---|---|---|---|
| 5,105,457 A | 4/1992 | Glassman | |
| 5,194,912 A | 3/1993 | Batchelder et al. | |
| 5,261,410 A | 11/1993 | Alfano et al. | |
| 5,293,872 A * | 3/1994 | Alfano et al. | 600/475 |
| 5,377,004 A | 12/1994 | Owen et al. | |
| 5,442,438 A | 8/1995 | Batchelder et al. | |
| 5,452,723 A * | 9/1995 | Wu et al. | 600/342 |
| 5,528,393 A | 6/1996 | Sharp et al. | |
| 5,623,342 A | 4/1997 | Baldwin et al. | |
| 5,689,333 A | 11/1997 | Batchelder et al. | |
| 5,710,626 A | 1/1998 | O'Rourke et al. | |
| 5,799,656 A | 9/1998 | Alfano et al. | |
| 5,862,273 A | 1/1999 | Pelletier | |
| 5,901,261 A | 5/1999 | Wach | |
| 5,911,017 A | 6/1999 | Wach et al. | |
| 6,002,476 A | 12/1999 | Treado | |
| 6,167,297 A | 12/2000 | Benaron | |
| 6,205,354 B1 * | 3/2001 | Gellermann et al. | 600/477 |
| 6,485,413 B1 * | 11/2002 | Boppart et al. | 600/160 |
| 2001/0052979 A1 | 12/2001 | Treado et al. | |
| 2001/0055462 A1 * | 12/2001 | Seibel | 385/147 |
| 2002/0113210 A1 | 8/2002 | Treado et al. | |
| 2003/0004419 A1 | 1/2003 | Treado et al. | |
| 2003/0114762 A1 * | 6/2003 | Balas et al. | 600/476 |
| 2003/0130579 A1 * | 7/2003 | McClane et al. | 600/476 |

\* cited by examiner

*Primary Examiner*—Brian L. Casler
*Assistant Examiner*—William C. Jung
(74) *Attorney, Agent, or Firm*—Duane Morris LLP

(57) ABSTRACT

Apparatus and methods for spatially resolved Raman detection of molecules indicative of the borders of lesions with normal tissue are disclosed. A region of biological tissue was illuminated with monochromatic light. A Raman shifted light signal is detected from endogenous molecules in the region, the molecules being spatially organized in a localized first area of the region. These molecules are indicative of a border between normal tissue and a lesion. The Raman shifted light signal is then spatially resolved in at least one direction.

47 Claims, 5 Drawing Sheets

METHOD FOR RAMAN CHEMICAL IMAGING OF ENDOGENOUS CHEMICALS TO REVEAL TISSUE LESION BOUNDARIES IN TISSUE

CROSS REFERENCE TO RELATED APPLICATIONS

This application claims priority pursuant to 35 U.S.C. 119(e) to U.S. Provisional Application No. 60/301,708 filed Jun. 28, 2001 which is incorporated herein by reference in its entirety including incorporated material.

FIELD OF THE INVENTION

The field of the invention is the field of tissue evaluation and, more particularly, the field of tissue evaluation using optical detection of light which has been Raman shifted in frequency.

BACKGROUND OF THE INVENTION

Cancer is the second leading cause of death in the United States and over 1.2 million people are diagnosed with this disease annually. Cancer is significant, not only in lives lost, but also in the $107 billion cost to the United States economy in 2000 according to the National Institutes of Health. It is widely recognized among the cancer research community, that there is a need to develop new tools to characterize normal, precancerous, cancerous, and metastatic cells and tissues at a molecular level. These tools are needed to help expand our understanding of the biological basis of cancers. Molecular analysis of tissue changes in cancer improve the quality and effectiveness of cancer detection and diagnosis strategies. The knowledge gained through such molecular analyses helps identify new targets for therapeutic and preventative agents.

Diagnosis of cancer is the first critical step to cancer treatment. Included in the diagnosis is the type and grade of cancer and the stage of progression. This information drives treatment selection. When cancer is suspected, a patient will have the tumor removed or biopsied and sent for histopathology analyses. Conventional handling involves the tissue undergoing fixation, staining with dyes, mounting and then examination under a microscope for analysis. Typically, the time taken to prepare the specimen is of the order of one day. The pathologist will view the sample and classify the tissue as malignant or benign based on the shape, color and other cell and tissue characteristics. The result of this manual analysis depends on the choice of stain, the quality of the tissue processing and staining, and ultimately on the quality of education, experience and expertise of the specific pathologist.

Early definitive detection and classification of cancerous growths is often crucial to successful treatment of this disease. Currently, several biopsy techniques are used as diagnostic methods after cancerous lesions are identified. In the case of breast cancer, lesions are typically identified with mammography or self breast exam. The most reliable method of diagnosis is examination of macroscopic-sized lesions. Macroanalysis is performed in conjunction with microscopic evaluation of paraffin-embedded biopsied tissue which is thin-sectioned to reveal microscale morphology.

The detection and diagnosis of cancer is typically accomplished through the use of optical microscopy. A tissue biopsy is obtained from a patient and that tissue is sectioned and stained. The prepared tissue is then analyzed by a trained pathologist who can differentiate between normal, malignant and benign tissue based on tissue morphology. Because of the tissue preparation required, this process is relatively slow. Moreover, the differentiation made by the pathologist is based on subtle morphological differences between normal, malignant and benign tissue based on tissue morphology. For this reason, there is a need for an imaging device that can rapidly and quantitively diagnose malignant and benign tissue.

Alternatives to traditional surgical biopsy include fine needle aspiration cytology and needle biopsy. These non-surgical techniques are becoming more prevalent as breast cancer diagnostic techniques because they are less invasive than biopsy techniques that harvest relatively large tissue masses. Fine needle aspiration cytology has the advantage of being a rapid, minimally invasive, non-surgical technique that retrieves isolated cells that are often adequate for evaluation of disease state. However, in fine needle biopsies intact breast tissue morphology is disrupted often leaving only cellular structure for analysis which is often less revealing of disease state. In contrast, needle biopsies use a much larger gauge needle which retrieve intact tissue samples that are better suited to morphology analysis. However, needle biopsies necessitate an outpatient surgical procedure and the resulting needle core sample must be embedded or frozen prior to analysis.

A variety of "optical biopsy" techniques have potential as non-invasive, highly sensitive approaches that will augment, or even be alternatives to current diagnostic methods for early detection of breast cancer. "Optical biopsies" employ optical spectroscopy to non-invasively probe suspect tissue regions in situ, without extensive sample preparation. Information is provided by the resultant spectroscopically unique signatures that may allow differentiation of normal and abnormal tissues. Despite years of research and development, two techniques that have not realized their potential are:

(1) fluorescence optical biopsies, which fails due to the nonspecific nature of tissue autofluorescence; and (2) near-infrared optical diagnostics, in particular non-invasive glucose sensing, which fails due to interference from tissue major components, including predominantly water.

In contrast to other techniques, Raman spectroscopy holds promise as an optical biopsy technique that is anticipated to be broadly applicable for characterization of a variety of cancerous disease states. A number of researchers have shown that Raman spectroscopy of masses of cells has utility in differentiating normal vs. malignant tissue and differentiating normal vs. benign tissue. In general, the Raman spectra of malignant and benign tissues show an increase in protein content and a decrease in lipid content versus normal breast tissue, demonstrating that cancer disease states impact the chemistry of the tissue.

However, Raman spectroscopy has not been able to differentiate benign vs. malignant tissues due to the spectral similarities of these tissue types. In addition, Raman spectroscopy of breast tissue samples requires large numbers of cell populations. If only a small portion of the cells are cancerous, as in the early stages of lesion development, then Raman spectroscopy of a large number of such cells will be insensitive to the disease. It would be advantageous to have a technique capable of the spatial sensitivity needed for discrimination of cancerous from normal cells in early stage breast cancer diagnosis.

Chemical imaging based on optical spectroscopy, in particular Raman spectroscopy, provides the clinician with important information. Chemical imaging simultaneously provides image information on the size, shape and distribution (the image morphology) of molecular chemical species present within the sample. By utilizing molecular-specific imaging, based on chemical imaging, the trained clinician can make a determination on the disease-state of a tissue or cellular sample based on recognizable changes in morphology without the need for sample staining or modification.

Apparatus for Raman Chemical Imaging (RCI) has been described by the inventors in U.S. Pat. No. 6,002,476, and in co-pending U.S. Non-provisional application 09/619,371 filed Jul. 19, 2000 which claims benefit of U.S. Provisional application 60/144,518 filed Jul. 19, 1999. The above identified U.S. patents, patent applications, and publications are hereby incorporated by reference.

OBJECTS OF THE INVENTION

It is an object of the invention to produce apparatus and methods using Raman shifted light for diagnosis of lesions in tissue. It is an object of the invention to produce apparatus and methods for diagnosis of tissue samples excised from a patient. It is an object of the invention to produce apparatus and methods for in vivo diagnosis of tissue. It is an object of the invention to produce apparatus and methods for finding a lesion in vivo in tissue. It is an object of the invention to produce apparatus and methods for determining the borders of lesions in vivo and in tissue samples excised from a patient. It is an object of the invention to produce apparatus and methods for spatially resolving Raman shifted light from tissue in vivo and in tissue samples. It is an object of the invention to produce apparatus and methods for imaging a lesion with light which has been Raman shifted.

SUMMARY OF THE INVENTION

Raman chemical imaging is used to differentiate between normal tissue and benign and malignant lesions. In particular, Raman chemical imaging is shown to be sensitive to calcified tissue and to carotenoid molecules. Carotenoid molecules are concentrated at the border of a lesion, and can be used to indicate the borders of the lesion. Spatially resolved Raman signals indicate lesions and borders of lesions. Other molecular species which may be indicative of border regions are noted.

DETAILED DESCRIPTION OF THE INVENTION

Raman Spectroscopy

Figure 1A:
FIG. 1A. Brightfield reflectance microscope image of a calcified lesion from a five micron thick frozen section biopsy.

When light interacts with matter, a portion of the incident photons are scattered in all directions. A small fraction of the scattered radiation differs in frequency (wavelength) from the illuminating light. If the incident light is monochromatic (single wavelength) as it is when using a laser source or other sufficiently monochromatic light source, the scattered light which differs in frequency may be distinguished from the light scattered which has the same frequency as the incident light. Furthermore, frequencies of the scattered light are unique to the molecular or crystal species present. This phenomenon is known as the Raman effect.

In Raman spectroscopy, energy levels of molecules are probed by monitoring the frequency shifts present in scattered light. A typical experiment consists of a monochromatic source (usually a laser) that is directed at a sample. Several phenomena then occur including Raman scattering which is monitored using instrumentation such as a spectrometer and a charge-coupled device (CCD). Similar to an infrared spectrum, a Raman spectrum reveals the molecular composition of materials, including the specific functional groups present in organic and inorganic molecules and specific vibrations in crystals. Raman spectrum analysis is useful because each resonance exhibits a characteristic 'fingerprint' spectrum, subject to various selection rules. Peak shape, peak position and the adherence to selection rules can also be used to determine molecular conformation information (crystalline phase, degree of order, strain, grain size, etc.). Unlike infrared spectroscopy, a single Raman spectrometer can be applied to the molecular characterization of organic and inorganic materials simultaneously. Other advantages of Raman over traditional infrared spectroscopy include the ability to analyze aqueous phase materials and the ability to analyze materials with little or no sample preparation. Deterrents to using Raman spectroscopy as opposed to infrared spectroscopy include the relatively weak nature of the Raman phenomenon and interferences due to fluorescence. In the past several years, a number of key technologies have been introduced into wide use that have enabled scientists to largely overcome the problems inherent to Raman spectroscopy. These technologies include high efficiency solid state lasers, efficient laser rejection filters, and silicon charge coupled device (CCD) detectors.

In Raman spectroscopy instruments, a linear CCD array is typically positioned at the exit focal plane of single stage, low f number Raman monochromators for efficient collection of dispersive Raman spectra. The monochromator disperses the Raman shifted light, and the CCD array typically produces a signal which is proportional to the intensity of the Raman signal vs wavelength.

Raman Chemical Imaging (RCI)

In many respects, Raman chemical imaging is an extension of Raman spectroscopy. Raman chemical imaging combines Raman spectroscopy and digital imaging for the molecular-specific analysis of materials. Much of the imaging performed since the development of the first Raman microprobes has involved spatial scanning of samples beneath Raman microprobes in order to construct Raman "maps" of surfaces. Historically, Raman imaging systems have been built using this so called flying spot ("point-scanning") approach, where a laser beam is focused to a spot and is scanned over the object field, or likewise a line scanning approach, where the laser spot is broadened in one direction by, for example, a cylindrical lens, and the two dimensional image formed on a CCD array has one spatial dimension and one wavelength dimension. Raman chemical imaging techniques have only recently achieved a degree of technological maturity that allows the simultaneous collection of high-resolution (spectral and spatial) data. Advancements in imaging spectrometer technology and their incorporation into microscopes that employ CCDs, holographic optics, lasers, and fiber optics have allowed Raman chemical imaging to become a practical technique for material analysis.

Imaging spectrometers include Fabry Perot angle rotated or cavity tuned liquid crystal (LC) dielectric filters, acousto-optic tunable filters, and other LC tunable filters (LCTF) such as Lyot Filters and variants of Lyot filters such as Solc filters and the most preferred filter, an Evan's split element liquid crystal tunable filter, which is described in the March (1999) issue of Analytical Chemistry on page 175A. Other preferred wavelength filtering means comprise polarization-independent imaging interferometers such as Michelson, Sagnac, Twynam-Green, and Mach-Zehnder interferometers.

References describing the above identified techniques that can be used to obtain chemical images include:

Fiber Array Filters (FAST)—M. P. Nelson, M. L. Myrick, Appl. Spectroscopy 53, 751–759, (1999);

Dielectric Interference filters—D Batchelder, C Cheng, W Muller, B Smith, Makromol Chem Macromol. Symp 46, 171, (1991);

AOTF—P. J. Treado, I. W. Levin, E. N. Lewis, Appl. Spectrosc. 46, 1211–1216, (1992);

Lyot—B. Lyot, C. R. Acad. Sci. 197:1593. (1933);

Fabry Perot—K. A. Christainsen, N. L. Bradley, M. D. Morris, R. V. Morrison, Appl. Spectrosc. 49, 120–1125, (1995);

Solc filter—A. Yariv & P. Yeh, Optical Waves in Crystals, (Wiley N.Y., 1984);

Michelson Interferometer—Sybil P. Parker, Optics Source Book, (McGraw-Hill, N.Y., 1988 p143);

Sagnac Interferometer—S. Spielman, K. Fesler, C. B. Eom, T. H. Geballe, M. Fejer and A Kapitulnik, Phys. Rev. Lett., 65, 123 (1990); and Twyman-Green Interferometer—M. Born and E. Wolf, Principles of Optics: Electromagnetic Theory of Propogation of Light, 6th Ed, (Pergamon Press, Oxford, 1980) pp 302–305.

Mach-Zehnder—James D. Ingle, Jr., and Stanley R Crouch, Spectrochemical Analysis, (Prentice Hall, Engelwood, N.J., 1988), p 83.

Raman chemical imaging is a versatile technique that is well suited to the analysis of complex heterogeneous materials. In a typical Raman chemical imaging experiment, a specimen is illuminated with monochromatic light, and the Raman scattered light is filtered by an imaging spectrometer which passes only a single wavelength range. The Raman scattered light may then be used to form an image of the specimen. A spectrum is generated corresponding to millions of spatial locations at the sample surface by tuning an imaging spectrometer over a range of wavelengths and collecting images intermittently. Changing the selected passband (wavelength) of the imaging spectrometer to another appropriate wavelength causes a different material to become visible. A series of such images can then uniquely identify constituent materials, and computer analysis of the image is used to produce a composite image highlighting the information desired. Although Raman chemical imaging is predominately a surface technique, depth-related information can also be obtained by using different excitation wavelengths or by capturing chemical images at incremental planes of focus. Contrast is generated in the images based on the relative amounts of Raman scatter or other optical phenomena such as luminescence that is generated by the different species located throughout the sample. Since a spectrum is generated for each pixel location, chemometric analysis tools such as correlation analysis, Principle Component Analysis (PCA) and factor rotation, including Multivariate Curve Resolution (MCR) can be applied to the image data to extract pertinent information otherwise missed by ordinary univariate measures. A spatial resolving power of approximately 250 nm has been demonstrated for Raman chemical imaging using visible laser wavelengths. This is almost two orders of magnitude better than infrared imaging which is typically limited to 20 microns due to diffraction. In addition, image definition (based on the total number of imaging pixels) can be very high for Raman chemical imaging because of the use of high pixel density detectors (often 1 million plus detector elements).

Applications of Raman chemical imaging range from the analysis of polymer blends, defect status analysis in semiconductor materials, inclusions in human breast tissue and the characterization of corrosion samples. RCI provides a potential solution for obtaining both qualitative and quantitative image information about molecular composition and morphology of breast lesions allowing a more accurate medical diagnosis than traditional imaging methods.

Breast Tissue Results

Figure 1B:
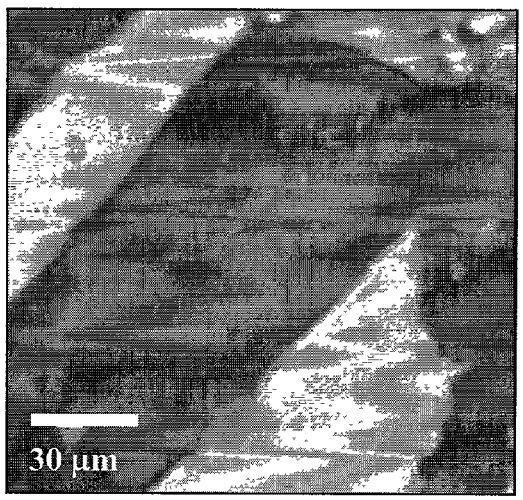
FIG. 1B. Magnified region indicated from FIG. 1A.
Figure 1C:
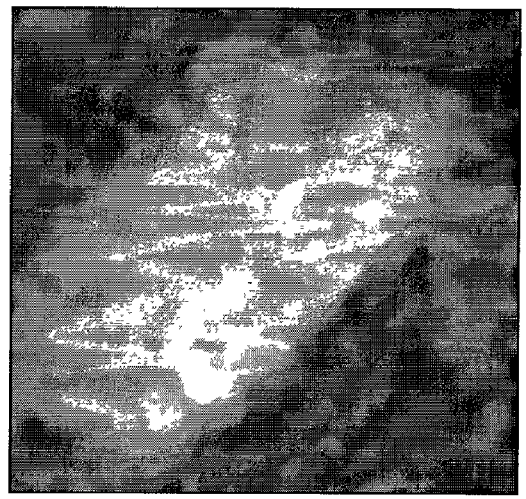
FIG. 1C. Raman Chemical Image (RCI) of the spatial distribution of calcification (calcium hydroxyapetite) and background (microscope slide)
Figure 2A:
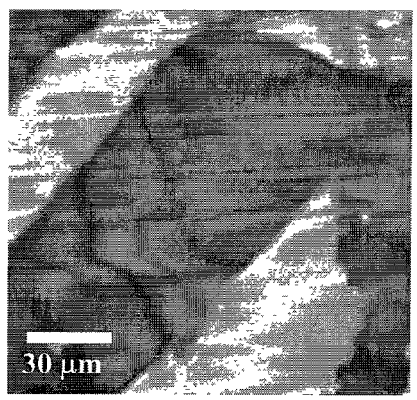
FIG. 2A. Brightfield reflectance microscope image of a region of calcified lesion as indicated in FIG. 1A.
Figure 2B:
FIG. 2B. Polarized light image of the region of interest indicated in FIG. 1A.
Figure 2C:
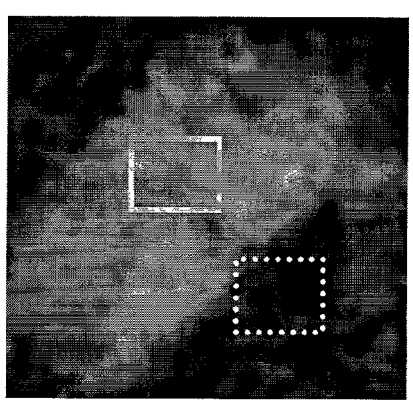
FIG. 2C. Raman Chemical Image (RCI) indicating calcified tissue.
Figure 2D:
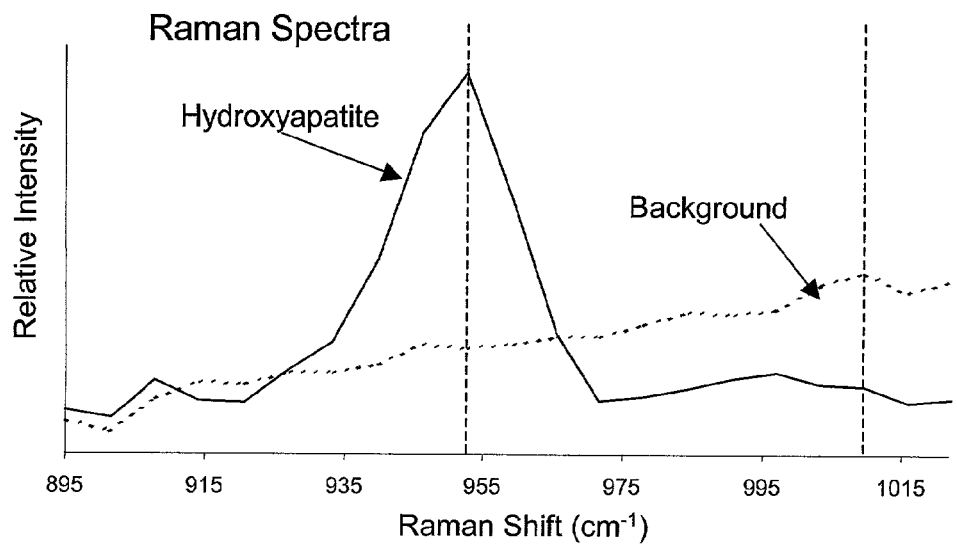
FIG. 2D. Raman spectral data from two regions of interest indicated in FIG. 2C showing the different chemical composition of these regions.

Raman spectra can potentially reveal a wealth of information about molecular properties of tissues. RCI compounds this information by allowing variations in these properties throughout the tissue to be probed. FIG. 1 shows RCI data on a calcified lesion. The tissue was excised from the patient, and frozen. A five micron thick section was sliced from the tissue and prepared on a microscope slide for imaging in a microscope. FIG. 1A shows a brightfield reflectance image of a portion of the frozen sectioned biopsy which is then magnified in FIG. 1B. The brightfield image reveals light and dark regions resulting from differences in refractive indices. These images, however, provide no insight into the molecular makeup of the tissues at hand. A Raman chemical image is shown in FIG. 1C and reveals the distribution of calcium hydroxyapatite based on its Raman response. FIG. 2A and FIG. 2B show dramatic differences in the optical microscopic image that depend on the polarization of the light. However, the Raman chemical image in FIG. 2C is unique in that it is derived from the distinct spectral Raman shown in FIG. 2D. The Raman spectra in FIG. 2D shows the spectral "fingerprints" associated with the calcium hydroxyapatite and the background, (the glass microscope slide) respectively. Such Raman spectra are the basis that allow a Raman Chemical image to be created. This ability to characterize calcifications is a critical issue in the diagnosis of breast carcinoma as calcification is a major element in mammographic evaluation and early cancer detection, and is critical for the diagnositic pathologist to identify. The Raman spectrum of calcium salts and protein calcium complexes is an incompletely explored area, in large part because of the previous unavailability of instrumentation capable of simultaneous high resolution spatial imaging and high wavelength resolution Raman spectrochemical analyses.

Difficulties exist when trying to use non imaging Raman spectroscopy alone to differentiate benign vs. malignant tissues due to the spectral similarities of these tissue types and to the spectrum of breast conditions that may mimic cancer. In addition, non imaging Raman spectroscopy of breast tissue samples large numbers of cell populations. If only a small portion of the cells are cancerous, as in the early stages of lesion development, then non-imaging Raman spectroscopy will be insensitive to the disease. It is very advantageous to have a technique capable of the spatial imaging sensitivity needed for discrimination of cancerous from normal cells in early stage breast cancer diagnosis.

Figure 3A:
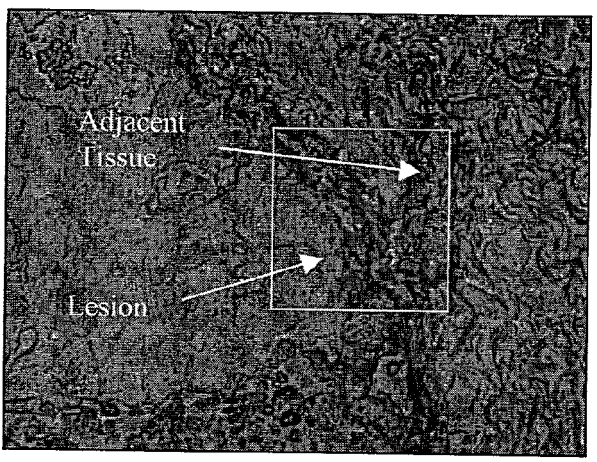
FIG. 3A. Brightfield reflectance microscope image of a 5 micron thin section of human breast tissue biopsy sample showing a lesion and the adjacent tissue.
Figure 3B:
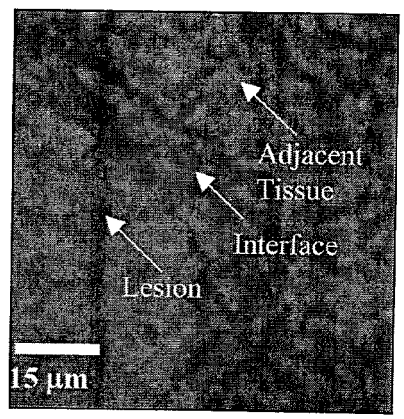
FIG. 3B. Magnified region of interest indicated in FIG. 3A.

We have developed an imaging optical biopsy approach based on Raman chemical imaging. In comparison with non-imaging Raman spectroscopy, our approach has the advantage that we efficiently collect spatial resolved Raman spectra so that morphometric analysis (characterization by size and shape) can be performed in conjunction with Raman spectral analysis. The additional morphology information is anticipated to add a critical component to the analysis of disease states, in part because it builds upon traditional cancer histopathology methods and could therefore be readily adopted by pathologists. FIG. 3A shows a brightfield image of a 5 □m thin section human breast tissue biopsy sample viewed under the microscope. An enlarged section of the lesion is indicated and magnified in FIG. 3B to show the border or interface between a tumor and normal tissue, where both cancerous and normal cells are visible. The Raman chemical image of a carotenoid molecule, β-carotene, shown in FIG. 3C reveals the location of the tumor and carotenoid molecules. Note that the carotenoid molecules are associated with the border between the lesion and the normal tissue. The LCTF-generated Raman spectra in FIG. 3D shows the spectral "fingerprints" associated with the tumor and the typical normal tissue, respectively. The ability to see this boundary with an inherent chemical within human tissue is a unique finding with potential biological and clinical significance relating to the objective screening and characterization of tumor margins.

Figure 3C:
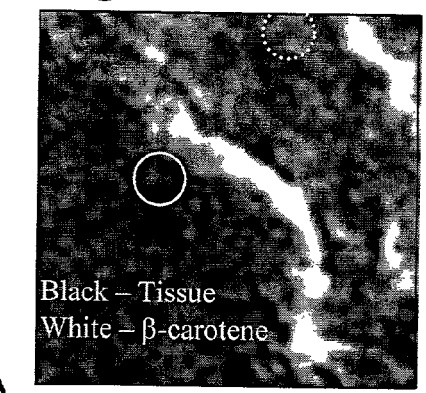
FIG. 3C. Raman Chemical Image (RCI) of the endogenous caroteniod (beta-carotene) that shows the border of the lesion.
Figure 3D:
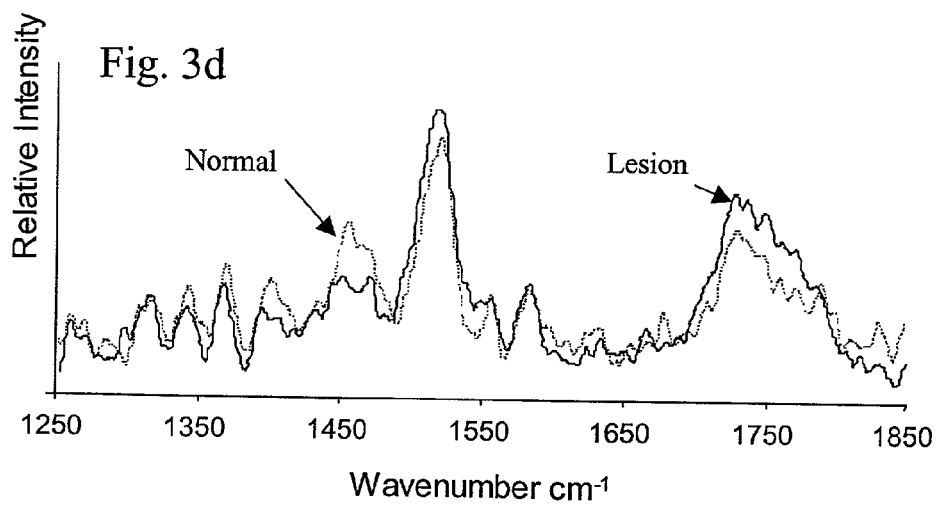
FIG. 3D. Raman spectra obtained with a tunable filter for two circled regions indicated in FIG. 3C.
Figure 4:
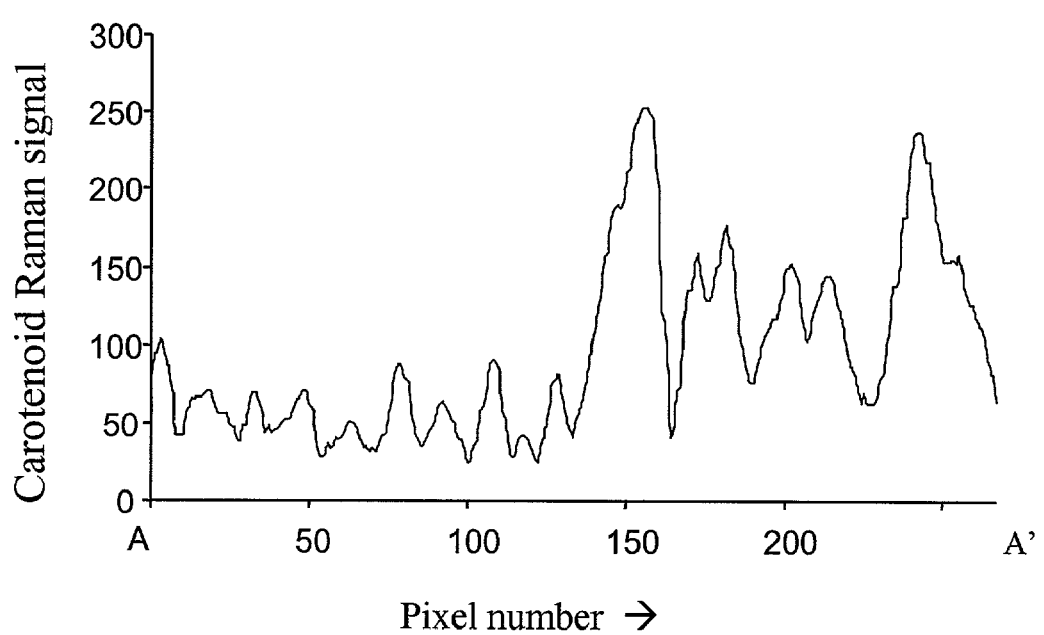
FIG. 4. Amount of carotenoid as determined from its spectral signal along the diagonal A–A' of the view shown in FIG. 1C.

FIG. 4 shows the results of a scan of the carotenoid signal along the diagonal A–A', ie along a line perpendicular to the tumor normal tissue boundary of FIG. 3C.

It is very important to know where the tumor margins are, and to know if the tumor has infiltrated beyond the a well defined boundary and into normal tissue. Detection of molecules indicative of the boundary is of great importance. The nutritional literature supports the idea that carotenoids are protective from cancer. It is surmised but not proven by the inventors that such protective molecules accumulate in the border region between a lesion and normal tissue, and act to prevent the lesion from growing. Other molecules suggested by the nutritional literature in relation to breast cancer are indoles, sulforaphanes, and flavonoids. Proteoglycans molecules have been noted to be associated with prostate cancer. With the Raman chemical imaging, the position of these molecules, and molecules which will be identified in the future, may be clearly imaged and used to show the extent and the stage of growth of the cancer or other lesion.

The cancerous cells shown in the lesion in FIGS. 3B and 3C are also differentiated from adjacent cells in the Raman image based on molecular compositional variations (lipid vs. protein content primarily) and can also be used to create a Raman image of the diseased tissue. As a result, the images are molecule-specific and more specific than images derived from stains. Because the Raman scattering of the tissues is intrinsic to the tissues, stains are not required and the technique is suitable for in vivo use. The Raman images are collected in only several seconds using laser power density that does not modify the tissue samples.

Figure 5:
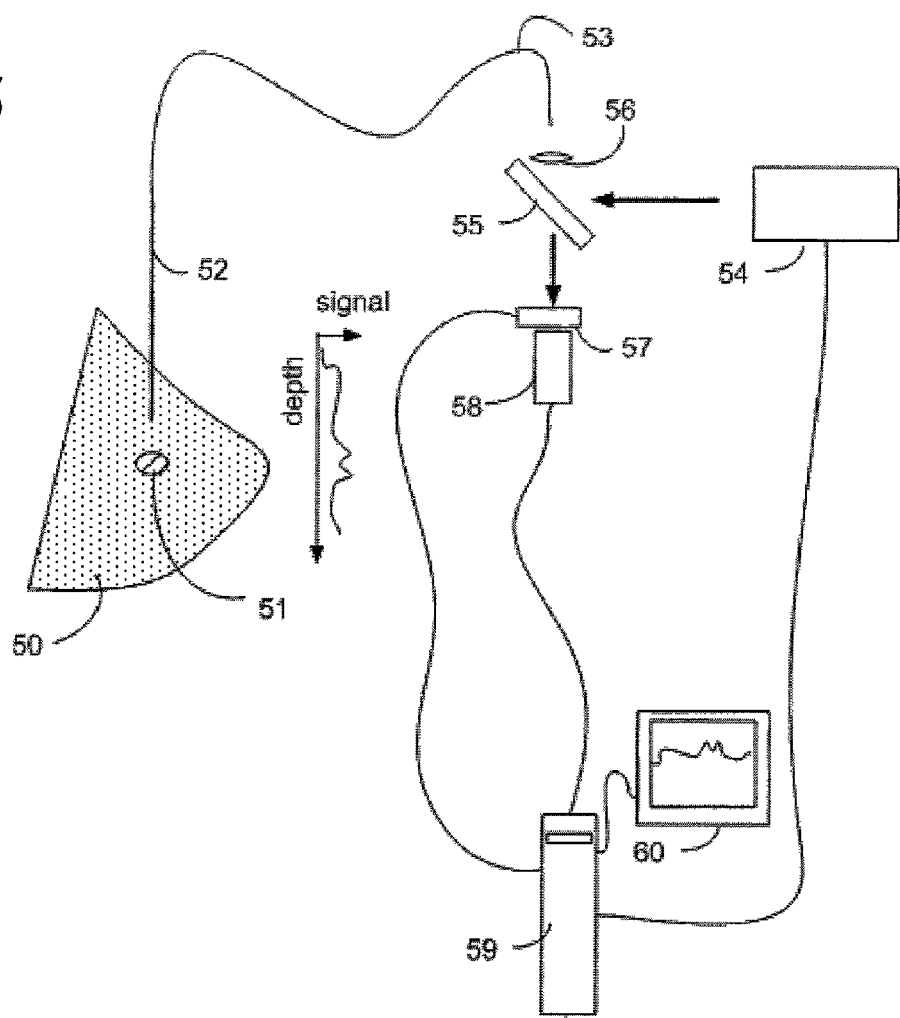
FIG. 5. Preferred embodiment of the invention.

An in vivo embodiment of the invention for examining a breast 50 or other non-arterial soft tissue for a lesion 51 is shown in FIG. 5. An endoscope or other instrument 52 is used to introduce light carried by an optical fiber 53 from a monochromatic light source 54. A dichroic mirror 55 and lens 56 are shown schematically for introducing the light into the fiber 53. Raman light from the breast is carried from the breast tissue back through the lens 56 and mirror 55, through a filter 57 to a detector 58. The signal from the detector 58 is analyzed by a computer system 59 and displayed on a monitor 60.

Filter 57 is most preferably a Evan's split element liquid crystal tunable filter, which is controlled by computer 59.

The endoscope 52 is preferably an imaging endoscope or fiberscope, where light is conducted from the breast tissue to the detector 58 in a coherent manner through a large plurality of optical fibers. A series of two dimensional images is preferably taken as a function of depth into the tissue and of the Raman shifted wavelength.

Results of a preferable embodiment of the invention is shown by an insert in FIG. 5, where the signal shown is a signal of a molecule indicative of a border region between the breast 50 or other non arterial soft tissue and the lesion 51. The spatially resolved signal of calcified tissue or of, for example, carotenoid molecules, is shown in the insert as a function of depth into the breast as the needle carrying the optical fiber is moved into the breast. The signal is shown displayed on the display device 60. In this embodiment, a much finer needle is used than the needle carrying an imaging endoscope. In the fine needle embodiment, the location of the lesion may be more accurately determined, so that fine needle aspiration cytology and/or needle core biopsy may be performed. In the fine needle embodiment, the filter 57 may be a normal spectrometer or a liquid crystal tunable filter, preferably of the Evan's split element type.

Raman chemical imaging also has demonstrated utility for the quantitative assessment of lesions in breast tissues. However, there is a need to make systematic strides in the development of a RCI optical biopsy. RCI of animal breast tissue models have been analyzed, as well as studies of human cancer lesions. Other lesions besides benign and malignant tumors, such as pockets of infection and inflamation will show up in the Raman chemical images. Several data treatment methods have been utilized to analyze the Raman image data which include band ratioing, band shift analysis, and classical linear least squares analysis. Comparisons have been made between the various processing approaches that address the utility of RCI for breast tissue component discrimination.

Applications

There is a great need for an instrument that can provide: real time detection with accuracy, decreased patient discomfort and recovery, minimal cosmetic defect of the breast, minimal distortion of the breast tissue that might make interpretation of future mammograms difficult and most importantly provide the patient with rapid feedback on her condition.

The user base for an instrument suitable for objective assessment of breast lesions of will consist of medical research laboratories, University and non-affiliated hospitals, and private clinics.

On another level, the customer or end-user is the patient that requires the procedure be completed to determine the disease state of her breast tissues. At this level the numbers are as follows: more than 1,000,000 biopsies were conducted in 1997; the growth rate for biopsies is almost 20% annually as clinicians struggle with how to determine the disease state of tissue early enough to prevent radical measures; the typical "customer" is a woman over the age of 40 that should be having annual breast exams by a clinician; and the number of potential customers is approximately 57 million (women between ages of 40 and 85).

The benefits to the target users of RCI systems will be substantial. Configured in an endoscopic version of the technology, RCI can be employed for "real-time" breast tissue evaluation tool that is compatible with and complementary to existing, mature clinical approaches (namely, needle core biopsies). When performed in combination the effectiveness of breast cancer diagnosis will likely be enhanced. Benefits will include, but are not limited to, the following:

- Real-time evaluation of suspicious lesions sites identified through self-breast exam and/or mammography that are made accessible via needle core biopsy.
- Immediate feedback to the clinician as to the severity of the clinical situation. Results can be communicated to the patient by the physician shortly after completion of Raman biopsy.
- Potential information on prognostic indicators of disease such as growth rate through quantitative evaluation of cellular nucleic acid composition and proliferation associated peptides.
- Minimal patient discomfort.
- Minimal to no cosmetic defect of the breast.
- Reduced exposure to ionizing radiation (x-rays).
- Specific applications of a RCI system for evaluating breast lesions will include the following:
- Discrimination of malignant vs. benign tumors
- Spatial distribution of carotenoids in tissues
- Spatial distribution of calcified tissue
- Spatial distribution of proteins, lipids and carbohydrates in tissues
- Advantages Over Currently Available Technology Traditional approaches to identification of breast lesions include self-breast exam and x-ray mammography. These techniques are effective as initial screening techniques, especially when performed in combination. Unfortunately, mammography is associated with a high false positive rate, resulting in 3–7 patients being biopsied for every patient cancer diagnosed. Although many mammographic abnormalities are definitely benign, and others are obviously malignant, there are many lesions in which the diagnosis cannot be made with certainty based on the mammographic appearance alone. To verify the disease-state of a detected lesion, tissue must be sampled for pathologic examination. This may be done with fine needle aspirates, core biopsies, or excisional biopsies. These samples are then prepared, stained, and inspected by a trained pathologist. This process can take several days to complete before the patient is informed of the outcome. Raman chemical imaging technology has the potential to assist diagnosis of the disease state of breast lesions in real-time.

Currently, several biopsy techniques are used as diagnostic methods after breast lumps are identified, typically with mammography, ultrasound, or breast examination. The most reliable method of diagnosis is examination of macroscopic-sized lesions. Macroanalysis is performed in conjunction with microscopic evaluation of paraffin-embedded biopsied tissue which is thin-sectioned to reveal microscale morphology.

Alternatives to traditional surgical biopsy include fine needle aspiration cytology and needle core biopsy. These non-surgical techniques are becoming more prevalent as breast cancer diagnostic techniques because they are less invasive than conventional biopsy techniques that involve surgical incision. Fine needle aspiration cytology has the advantage of being a rapid, minimally invasive, non-surgical technique that retrieves cytologic material that is often adequate for evaluation of disease state. However, in fine needle biopsies breast tissue histologic features are minimal, leaving only cytologic features for analysis of disease state. In contrast, needle biopsies use a much larger gauge needle which retrieve tissue samples that are better suited to morphology analysis. However, needle biopsies necessitate an outpatient surgical procedure and the resulting needle core sample must be fixed, embedded and processed prior to analysis.

State-of-the-Art Raman Chemical Imaging Techniques

Several Raman chemical imaging technologies have evolved that compete with widefield tunable filter-based RCI. These techniques include point scanning RCI, line imaging RCI, RCI using interference filters, Fourier-transform interferometry, Hadamard-transform scanning and FAST technology.

Point scanning involves taking a complete spectrum for a single X,Y position of a sample followed by raster-scanning the sample for the remaining X,Y positions. This method offers advantages of high spectral resolution and full spectral resolution, but lacks high image definition capabilities and is extremely time consuming. Line imaging involves collecting data from vertical sections of the sample characterized by a single value of X and all values of Y, followed by subsequent scanning in the X direction. This method has the nearly the same advantages and disadvantages as the point scanning approach, but can be done more rapidly. Field curvature artifacts are a consequence of line imaging which degrade image quality. The use of single or multiple interference filters can be used to produce a wavelength specific image(s). This method is rapid, cheap and produces high definition images, but lacks spectral resolution and is susceptible to image artifacts. Fourier-transform interferometers use a mechanically driven interferometer with a CCD-based detection system. Interferograms are imaged with the CCD for subsequent spectral interpretation for each step of the interferometer. This method boasts good spatial resolution but suffers from poor spectral resolution (~100 cm$^{-1}$). Hadamard transform chemical imaging techniques couple Hadamard mask spatial multiplexing with CCD-based detection to obtain two spatial and one spectral dimension of data. This method offers S/N advantages for low-light level applications such as Raman spectroscopy in addition to sub-nanometer spectral resolution. However, the technique suffers from fair spatial resolution and poor temporal resolution since the latter involves scanning through numerous coding masks. Fiber array spectral translators (FAST) use a two dimensional arrangement of Raman collection fibers which are drawn into a one dimensional distal array at the opposite end. The one dimensional fiber stack is coupled to an imaging spectrograph. Software then extracts the spectral/spatial information which is embedded in a single CCD image frame. FAST is capable of acquiring thousands of full spectral range, position-specific Raman spectra and wavenumber-specific Raman chemical images in seconds. However, the image definition of FAST is limited by the number of pixels in any one direction of the CCD chip used in the detection system (typically no better than 45×45 (~2048) imaging elements).

The ideal chemical imaging system for characterization would provide fast acquisition times (seconds), high spatial resolution (sub-micron) and good spectral resolution (<0.2 nm). To date, systems equipped with liquid crystal tunable filters are the only RCI system that meets these requirements.

Other Spectroscopy-Based Imaging Methods

Spectroscopic technologies that compete with Raman such as fluorescence and infrared (IR) spectroscopy are not of great concern based on the resolution needed to see molecules on the order of 250 microns. Although fluorescence has showed some promise, it suffers from low specificity without the use of invasive dyes or stains that require FDA approval. IR spectroscopy cannot compete due to the difficulty with water absorption in the IR. Tissues do not image well because of their aqueous nature. Systems equipped with LCTFs surpass any dispersive grating or acousto-optic tunable filter (AOTF) technology on the market. The spectral bandpass capability of the LCTF is 8 cm$^{-1}$ allowing for the most effective means to obtain image detail.

Traditional Biomedical Imaging Methods

Traditionally, biomedical imaging has been divided into capturing images of live tissue (in vivo) at relatively low resolution (from 10 to 1000 microns) and capturing images of excised tissue at high resolution. In vivo imaging is usually performed using non-optical modalities such as magnetic resonance imaging, ultrasound, or x-ray tomography, which assess the general shape and appearance of tissue in its native state; however, this approach does not provide the cellular resolution necessary to analyze cell types and tissue morphology. To image tissue at high resolution using conventional optical or electron microscopes, one had to slice the tissue into thin sections, otherwise the tissue above and below the layer of interest will produce out-of-focus reflections that seriously degrade image contrast. Confocal techniques address this to some extent. Excising, fixing and staining thin tissue sections is however static, is time-consuming and by the very nature of the process involves tissues which have been rendered non viable.

A RCI system will produce quantitative digital images of the lesion tissue that will be recognizable to the clinician who makes disease-state determinations, in large part, based on the visual appearance of images. The appearance of suspect tissue, when viewed by the naked eye if lesions are large enough, or via x-ray mammography, or via magnetic resonance imaging (MRI) provides important clues to the state of the tissue. After years of training, clinicians can base diagnosis on these subtle visual clues. Despite the best efforts of highly skilled professionals, early stage disease-state determination is a difficult problem. By aiding the pathologist with an image that maps the distribution of certain molecular species, the large number of subjective determinations of disease state in breast tissue biopsies can be greatly reduced.

Although we have described certain present preferred embodiments of our method for objective evaluation of breast tissue using Raman imaging spectroscopy, it should be distinctly understood that our invention is not limited thereto, but may include equivalent methods. It is further to be distinctly understood that the present invention is not limited to the evaluation of breast tissue and applies to the evaluation of all tissue. Obviously, many modifications and variations of the present invention are possible in light of the above teachings. It is therefore to be understood that, within the scope of the appended claims, the invention may be practiced otherwise than as specifically described. Publications, patents, and patent applications noted herein are hereby included by reference.

We claim:

1. A method for detecting a border between normal tissue and a lesion which comprises
   a) illuminating a region of biological tissue with monochromatic light;
   b) detecting Raman shifted light from endogenous molecules in the region with a Raman chemical imagining spectrophotometer, wherein the molecules are indicative of a border between normal tissue and a lesion; and
   c) spatially resolving the Raman shifted light signal in at least one direction to produce a Raman chemical image indicative of a border between the normal tissue and the lesion in said at least one direction.

2. The method of claim 1, wherein a two-dimensional chemical image of the region is produced.

3. The method of claim 2, where the Raman shifted light from the region passes through a FAST fiber array spectral translator.

4. The method of claim 2, where the Raman shifted light from the region passes through a Fabry Perot tunable filter.

5. The method of claim 2, where the Raman shifted light from the region passes through an acousto-optic tunable filter.

6. The method of claim 2, where the Raman shifted light from the region passes through a liquid crystal tunable filter.

7. The method of claim 6, where the Raman shifted light from the region passes through a Lyot filter.

8. The method of claim 7, where the Raman shifted light from the region passes through an Evan's split element liquid crystal tunable filter.

9. The method of claim 7, where the Raman shifted light from the region passes through a Solc filter.

10. The method of claim 2, where the Raman shifted light from the region passes through a polarization-independent imaging interferometer.

11. The method of claim 10, where the Raman shifted light from the region passes through a Michelson interferometer.

12. The method of claim 10, where the Raman shifted light from the region passes through a Sagnac interferometer.

13. The method of claim 10, where the Raman shifted light from the region passes through a Twynam-Green interferometer.

14. The method of claim 10, where the Raman shifted light from the region passes through a Mach-Zehnder interferometer.

15. The method of claim 2, where the molecules are chosen form the group consisting of indoles, sulforaphanes, carotenoids, proteoglycans and flavonoids.

16. The method of claim 15, where the molecules are carotenoid molecules.

17. The method of claim 15, where the molecules are indole molecules.

18. The method of claim 15, where the molecules are sulforaphane molecules.

19. The method of claim 15, where the molecules are flavonoid molecules.

20. The method of claim 15, where the molecules are proteoglycan molecules.

21. The method of claim 2, where the region is prepared for illumination, in a step previous to step a), by excision of the tissue and by placing a specimen prepared from the tissue in position for illumination and imaging, wherein the tissue is not treated with staining agents.

22. The method of claim 2, where the region is prepared for illumination, in a step previous to step a), by excision of the tissue and by placing a specimen prepared from the tissue in position for illumination and imaging, wherein the tissue is treated with staining agents.

23. The method of claim 1, wherein said region is illuminated in vivo with monochromatic light introduced via an endoscope.

24. The method of claim 23, wherein a two-dimensional chemical image of the region is produced.

25. The method of claim 24, where the Raman shifted light from the region passes through a FAST fiber array spectral translator.

26. The method of claim 24, where the Raman shifted light from the region passes through a Fabry Perot tunable filter.

27. The method of claim 24, where the Raman shifted light from the region passes through an acousto-optic tunable filter.

28. The method of claim 24, where the Raman shifted light from the region passes through a liquid crystal tunable filter.

29. The method of claim 28, where the Raman shifted light from the region passes through a Lyot filter.

30. The method of claim 29, where the Raman shifted light from the region passes through an Evan's split element liquid crystal tunable filter.

31. The method of claim 24, where the Raman shifted light from the region passes through a polarization-independent imaging interferormeter.

32. The method of claim 31, where the Raman shifted light from the region passes through a Michelson interferometor.

33. The method of claim 31, where the Raman shifted light from the region passes through a Sagnac interferometer.

34. The method of claim 31, where the Raman shifted light from the region passes through a Twynam-Green interferometer.

35. The method of claim 31, where the Raman shifted light from the region passes through a Mach-Zehnder interferometer.

36. The method of claim 23, where the molecules are chosen form the group consisting of indoles, sulforaphanes, carotenoids, proteoglycans and flavonoids.

37. The method of claim 36, where the molecules are carotenoid molecules.

38. The method of claim 23, where a non-imaging endoscope is moved through the tissue in vivo, and the Raman shifted light signal is spatially resolved as the endoscope is moved through the tissue.

39. The method of claim 23, where the Raman shifted light from the region passes through an Evan's split element liquid crystal tunable filter.

40. The method of claim 23, wherein the endoscope is moved through the tissue to obtain a Raman chemical image from more then one region of said tissue.

41. The method of claim 40, wherein a two-dimensional chemical image is produced for each region of said tissue.

42. The method of claim 41, wherein said two-dimensional chemical images represent a series of images taken as a function of depth of the tissue.

43. The method of claim 41, wherein said multiple regions are in series as a function of depth of the tissue.

44. A method of performing an optical biopsy which comprises
  a) illuminating multiple regions of biological tissue in viva with monochromatic light introduced via an endoscope;
  b) detecting Raman shifted light from endogenous molecules in each region with a Raman chemical imaging spectrophotometer, wherein the molecules are indicative of a border between normal tissue and a lesion;
  c) spatially resolving the Raman shifted light signal in two dimensions for each region to produce a Raman chemical image of said tissue in two dimensions; and
  d) determining the location of any lesion in said tissue.

45. A biopsy method which comprises
  a) obtaining the Raman chemical image of biological tissue according to the method of claim 44; and
  b) performing a needle core biopsy of tissue in or around said lesion.

46. The method of claim 45, wherein said multiple regions are in series as a function of depth of the tissue.

47. The method of claim 46 which further comprises examining said biopsied tissue for signs of cancer.

* * * * *